(12) United States Patent
Nakayama

(10) Patent No.: US 10,973,399 B2
(45) Date of Patent: Apr. 13, 2021

(54) LIGHT SOURCE DEVICE FOR ENDOSCOPE

(71) Applicant: OLYMPUS CORPORATION, Tokyo (JP)

(72) Inventor: Noboru Nakayama, Iruma (JP)

(73) Assignee: OLYMPUS CORPORATION, Tokyo (JP)

( * ) Notice: Subject to any disclaimer, the term of this patent is extended or adjusted under 35 U.S.C. 154(b) by 335 days.

(21) Appl. No.: 16/059,094

(22) Filed: Aug. 9, 2018

(65) Prior Publication Data

US 2018/0368671 A1    Dec. 27, 2018

Related U.S. Application Data

(63) Continuation of application No. PCT/JP2017/000572, filed on Jan. 11, 2017.

(30) Foreign Application Priority Data

Mar. 7, 2016  (JP) ................. 2016-043616

(51) Int. Cl.
*A61B 1/00* (2006.01)
*A61B 1/06* (2006.01)
*G02B 23/26* (2006.01)
*G02B 23/24* (2006.01)
(Continued)

(52) U.S. Cl.
CPC ........ *A61B 1/0676* (2013.01); *A61B 1/00172* (2013.01); *A61B 1/0638* (2013.01); *A61B 1/0669* (2013.01); *A61B 5/0062* (2013.01); *A61B 5/0084* (2013.01); *G02B 23/2469* (2013.01); *G02B 23/26* (2013.01); *A61B 1/07* (2013.01)

(58) Field of Classification Search
None
See application file for complete search history.

(56) References Cited

U.S. PATENT DOCUMENTS

2002/0016620 A1    2/2002  Tsujita
2011/0015528 A1    1/2011  Kobayashi
2014/0303441 A1*  10/2014  Sakai ................ A61B 1/00057
                                                           600/160

FOREIGN PATENT DOCUMENTS

EP      3114984 A1    1/2017
JP   2002-045329 A    2/2002
JP   2011-019706 A    2/2011
(Continued)

OTHER PUBLICATIONS

International Search Report dated Mar. 14, 2017 issued in PCT/JP2017/000572.

*Primary Examiner* — Timothy J Neal
(74) *Attorney, Agent, or Firm* — Scully, Scott, Murphy & Presser, P.C.

(57) ABSTRACT

R, G, B laser beams emitted from an R_LD, a G_LD, and a B_LD, respectively, are divided, through demultiplexers, into respective monitoring laser beams and respective irradiation laser beams to be applied to a scanning type endoscope side. R, G, B drive currents for causing light emission at the R_LD, the G_LD, and the B_LD are controlled such that the light quantities of the divided monitoring laser beams become equal to monitoring light quantity values on which the division ratios in the case of temperature change are reflected. As a result of this control, the light quantities of the irradiation laser beams each fall within a range satisfying a predetermined condition.

12 Claims, 11 Drawing Sheets

(51) Int. Cl.
*A61B 5/00* (2006.01)
*A61B 1/07* (2006.01)

(56) References Cited

FOREIGN PATENT DOCUMENTS

JP 2015-019816 A 2/2015
WO WO 2016/027484 A1 2/2016

* cited by examiner

FIG. 4

| TEMPERATURE | 25°C | ... | 40°C | ... |
|---|---|---|---|---|
| R DIVISION RATIO (n_R) | 0.20 | ... | 0.30 | ... |
| G DIVISION RATIO (n_G) | 0.15 | ... | 0.30 | ... |
| B DIVISION RATIO (n_B) | 0.10 | ... | 0.30 | ... |

MAXIMUM PEAK LIGHT QUANTITY VALUE

MAXIMUM AVERAGE LIGHT QUANTITY VALUE

LIGHT EMISSION VALUE IN INITIAL STATE (AFTER WB ADJUSTMENT)

LIGHT SOURCE DEVICE FOR ENDOSCOPE

CROSS REFERENCE TO RELATED APPLICATION

This application is a continuation application of PCT/JP2017/000572 filed on Jan. 11, 2017 and claims benefit of Japanese Application No. 2016-043616 filed in Japan on Mar. 7, 2016, the entire contents of which are incorporated herein by this reference.

BACKGROUND OF THE INVENTION

1. Field of the Invention

The present invention relates to a light source device for an endoscope, which emits a laser beam to a scanning type endoscope.

2. Description of the Related Art

An endoscope using an image pickup device has been widely adopted in a medical field and others. In recent years, various types of scanning type endoscopes which guide, through an optical fiber, a laser beam generated by a light source device and scan with the laser beam for irradiating a site to be inspected, have been proposed. In the scanning type endoscope, use of an optical fiber offers an advantage that a diameter of an insertion portion can be reduced and the endoscope can be inserted in a thin tube-like site such that observation and inspection can be performed.

In this case, in order to use laser beams, the maximum light quantity and the total light quantity, in a fixed time period, of laser beams emitted from the light source device to the scanning type endoscope which is external to the light source device need to satisfy the laser safety standards.

For example, in a fifth embodiment (FIG. 7) of Japanese Patent Application Laid-Open Publication No. 2015-19816 as a conventional example, red, green, and blue laser beams emitted from a semiconductor light source are multiplexed by a multiplexer, a part of the multiplexed laser beam proportional to the entire output thereof is demultiplexed by a demultiplexer, the light quantity of the demultiplexed part of the output is detected by a light quantity monitor, an output from the light quantity monitor is outputted to a system controller, and the system controller monitors the intensity of a laser beam (illumination light) to be outputted to an optical fiber through which the laser beam is to be guided in the endoscope. Japanese Patent Application Laid-Open Publication No. 2015-19816 further discloses maintaining the intensity of illumination light so as to satisfy the laser safety standards. Further, in this conventional example, a temperature sensor is provided to a connection portion of the main body thereof, and the output from the temperature sensor is outputted to the system controller, and the system controller enables management of the temperature of the connection portion of the main body.

SUMMARY OF THE INVENTION

A light source device for an endoscope according to one aspect of the present invention includes:

a first light emitting element configured to emit a first laser beam of a first spectrum responding to a first control signal;

a second light emitting element configured to emit a second laser beam of a second spectrum responding to a second control signal;

a beam combiner which the first laser beam and the second laser beam enter, the beam combiner being configured to transmit a laser beam having a spectrum component based on a synthesized spectrum of the first spectrum and the second spectrum, and emit the laser beam as irradiation light to the endoscope, and to emit a part of the laser beam as monitoring light having an intensity at a predetermined division ratio;

a temperature measuring section configured to measure a temperature of the beam combiner; and a light emission control section including a memory holding a parameter regarding the division ratio at a plurality of temperatures, the light emission control section being configured to perform control, by outputting the first control signal and the second control signal based on the parameter corresponding to the temperatures, such that a maximum light quantity of the irradiation light satisfies a predetermined condition.

BRIEF DESCRIPTION OF THE DRAWINGS

FIG. 4 is a diagram showing, in a table form, information about division ratios at demultiplexers at a plurality of temperatures stored in a memory;

DETAILED DESCRIPTION OF THE PREFERRED EMBODIMENTS

Hereinafter, embodiments of the present invention are described with reference to the drawings.

First Embodiment

Figure 1:
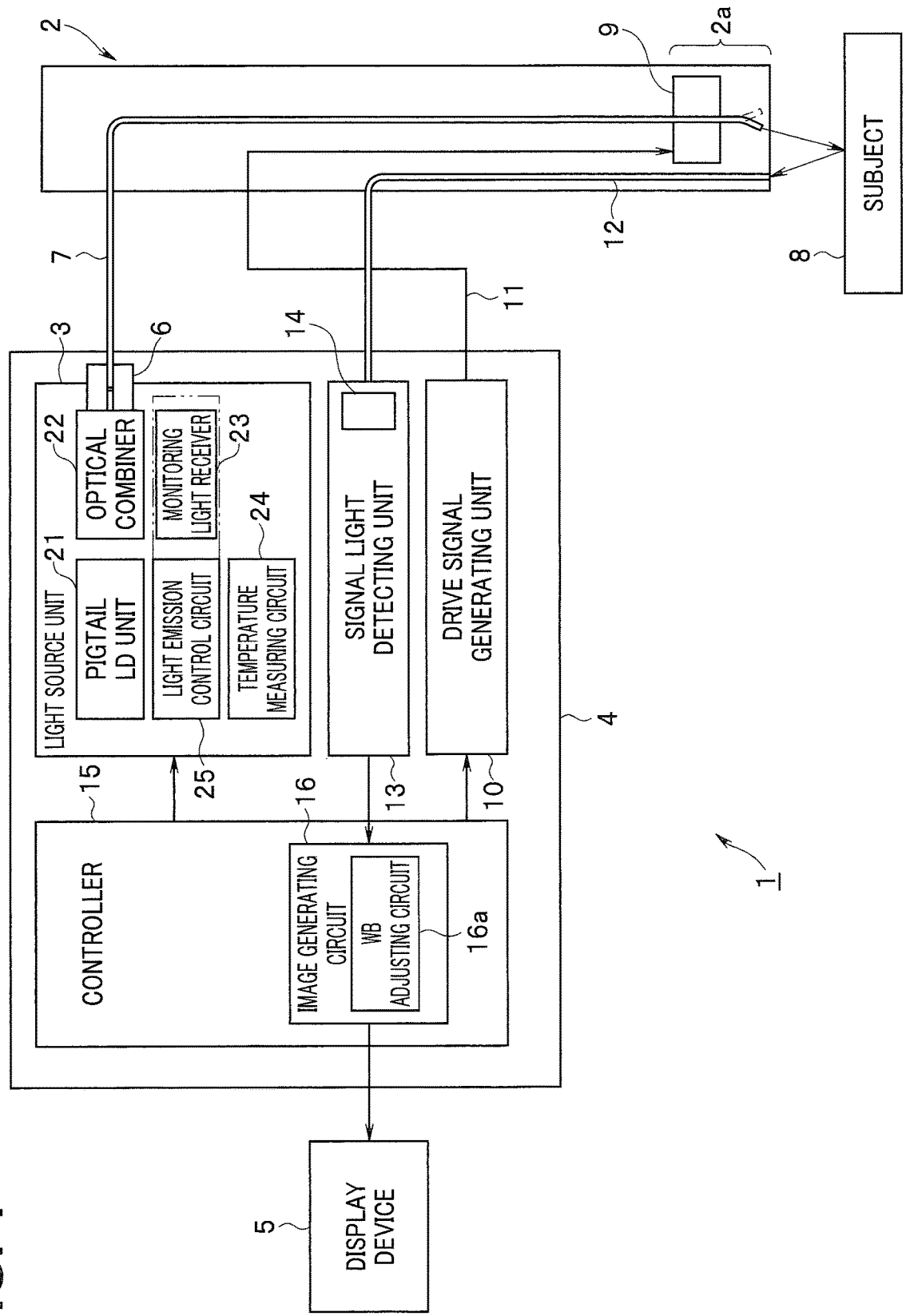
FIG. 1 is a diagram showing the entire configuration of a scanning type endoscope apparatus.

As illustrated in FIG. 1, a scanning type endoscope apparatus 1 includes a scanning type endoscope 2 which scans with irradiation light (or illumination light), a body device (or scanning type endoscope control device) 4 to which the scanning type endoscope 2 is attachably/detachably connected and in which a light source unit 3 forming an endoscope light source device of the first embodiment is incorporated, and a display device 5 which displays an image of image signals generated by the body device 4.

Irradiation light emitted from an optical connector 6 of the light source unit 3 enters a proximal end of an optical fiber 7 forming a light guide section of the scanning type endoscope 2 connected to the optical connector 6. Irradiation light having entered the proximal end of the optical fiber 7 is guided (transmitted) through the optical fiber 7, and is emitted from a distal end surface of the optical fiber 7 via a lens (not illustrated), and a subject 8 is irradiated with the emitted irradiation light.

A distal end portion 2a of the scanning type endoscope 2 is provided with a scanning section (or scanner) 9 which, upon application of a drive signal thereto, oscillates the distal end of the optical fiber 7 in two directions orthogonal to the longitudinal direction. In addition, irradiation light emitted from the oscillating distal end of the optical fiber 7 scans, along a spiral trajectory, over the subject 8.

A drive signal generating unit 10 provided in the body device 4 applies a generated drive signal to the scanning section 9 via a drive line 11.

Reflection light reflected by the subject 8 is incident on a distal end surface of a light receiving optical fiber 12. The reflection light incident on the distal end surface is guided (transmitted) to a proximal end of the light receiving optical fiber 12, and is emitted as signal light (or detection light) from the proximal end. The signal light emitted from the proximal end is received by an optical detector 14 of a signal light detecting unit 13 provided in the body device 4 so as to face the proximal end, and undergoes photoelectric conversion. The detection signal having undergone the photoelectric conversion by the optical detector 14 is further converted into a digital detection signal by an A/D converter (not illustrated), and then, is inputted into an image generating circuit 16 in a controller 15.

The image generating circuit 16 generates, from the inputted detection signal, an image signal in the case of scanning the subject 8 along the spiral trajectory, and outputs the generated image signal to the display device 5.

The image generating circuit 16 has a white balance adjusting circuit (abbreviated as "WB adjusting circuit" in FIG. 1) 16a that performs white balance adjustment to make an image to be displayed on the display device 5 white when the subject 8 is white. The white balance adjusting circuit 16a performs adjustment to obtain a white balance state by adjusting the respective gains of (variable gain) amplifiers that amplify red (R), green (G), and blue (B) image signal components (color signals) forming a color image signal.

Figure 2:
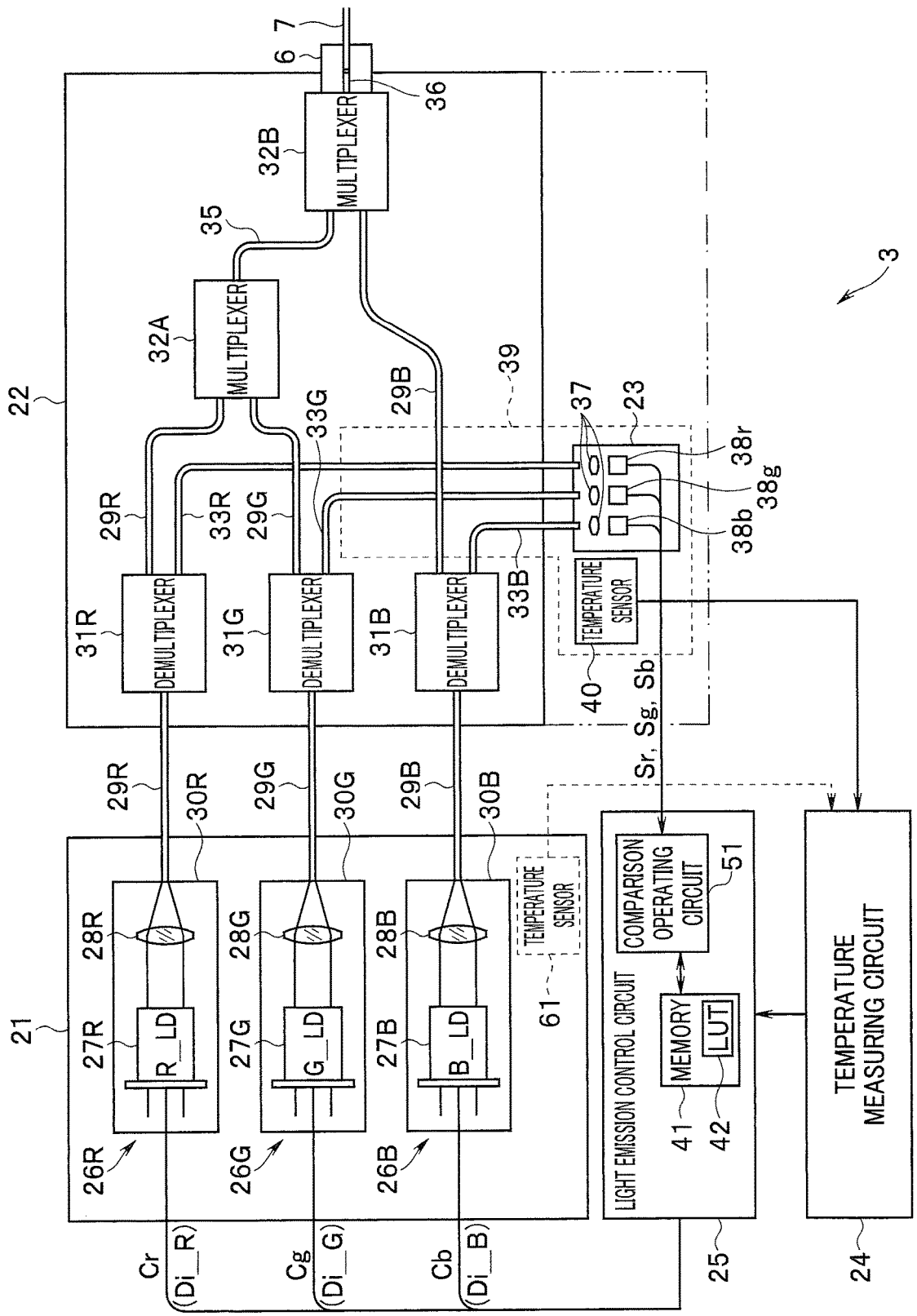
FIG. 2 is a diagram showing the configuration of a light source unit in a first embodiment of a light source device for an endoscope of the present invention.

FIG. 2 illustrates a detailed configuration of the light source unit 3. The light source unit 3 includes: a pigtail laser diode unit (abbreviated as "pigtail LD unit") 21 which emits, inside the light source unit 3, laser beams within R, G, B wavelength regions; an optical combiner 22 which guides (transmits) the R laser beam, the G laser beam, and the B laser beam (transmitted) from the pigtail LD unit 21 and emits irradiation light and monitoring light; a monitoring light receiver 23 which receives the monitoring light (emitted inside the light source unit 3); a temperature measuring circuit 24 for measuring the temperature of an area near the optical combiner 22; and a light emission control circuit 25 which controls, in accordance with the temperature measured by the temperature measuring circuit 24, the light quantity of light generated (emitted) by the pigtail LD unit 21. Further, the light source unit 3 includes, at a site where the optical combiner 22 emits irradiation light, the optical connector 6 to which the proximal end of the optical fiber 7 of the scanning type endoscope 2 is attachably/detachably connected. FIG. 2 illustrates the configuration example in which the monitoring light receiver 23 is disposed outside the optical combiner 22. However, the optical combiner 22 may include the monitoring light receiver 23, as indicated by a two-dot chain line.

The optical combiner 22 forming a beam combiner emits the irradiation light to the outside of the light source unit 3, and emits the monitoring light to the monitoring light receiver 23 within the light source unit 3. Therefore, no monitoring light is emitted to the outside of the light source unit 3 (accordingly, the light quantity (power or intensity) of the irradiation light emitted from the optical combiner 22 is set so as to satisfy the condition of the laser safety standards).

The pigtail LD unit 21 includes an R pigtail LD 26R which emits an R laser beam, a G pigtail LD 26G which emits a G laser beam, and a B pigtail LD 26B which emits a B laser beam.

The R pigtail LD 26R includes an R_LD 27R which serves as an R generating element for generating an R laser beam having a spectrum within an R wavelength region, a lens 28R which collects the R laser beam generated by the R_LD 27R, a light guiding optical fiber 29R having a proximal end which the R laser beam collected by the lens 28R enters, and a pigtail 30R which serves as a connection member for connecting the R_LD 27R and the lens 28R to the optical fiber 29R.

The configurations of the G pigtail LD 26G and the B pigtail LD 26B are obtained by replacing the R laser beam in the configuration of the R pigtail LD 26R with a G laser beam having a spectrum within a G wavelength region and a B laser beam having a spectrum within a B wavelength region, respectively.

Therefore, when J (J=R, G, B) is used, the following expression is possible: a pigtail LD 26J includes a J_LD 27J which serves as a J generating element for generating a J laser beam having a spectrum within a J wavelength region, a lens 28J which collects the J laser beam generated by the J_LD 27J, a light guiding optical fiber 29J having a proximal end which the J laser beam collected by the lens 28J enters, and a pigtail 30J which serves as a connection member for connecting the J_LD 27J and the lens 28J to the optical fiber 29J.

The J_LD 27J and the lens 28J may be integrated. The pigtail refers to a connection member for connecting the J_LD 27J (and the lens 28J) to the optical fiber 29J.

The optical fibers 29R, 29G, 29B guide the R laser beam, the G laser beam, and the B laser beam having entered the proximal ends thereof to the distal end surfaces thereof, respectively. At demultiplexers 31R, 31G, 31B in the optical combiner 22, the R laser beam, the G laser beam, and the B laser beam having entered the proximal ends of the optical fibers 29R, 29G, 29B are each demultiplexed or divided into two laser beams by a predetermined light quantity ratio (intensity ratio or power ratio) while maintaining the respective spectrums unchanged.

More specifically, the demultiplexer 31R divides the R laser beam incident thereon into a monitoring laser beam (also referred to as monitoring light) M_R of a division ratio n_R, which is a light quantity (or intensity) ratio for light dividing, and an irradiation laser beam (also referred to as irradiation light) I_R of a division ratio 1−n_R.

The irradiation laser beam I_R guided through the optical fiber 29R via the demultiplexer 31R enters a first multiplexer 32A. The monitoring laser beam M_R guided through the optical fiber 33R via the demultiplexer 31R enters the monitoring light receiver 23.

The demultiplexer 31G divides the G laser beam having entered the proximal end of the optical fiber 29G into a monitoring laser beam (also referred to as monitoring light) M_G of a division ratio n_G and an irradiation laser beam (also referred to as irradiation light) I_G of a division ratio 1−n_G. The irradiation laser beam I_G guided through the optical fiber 29G via the demultiplexer 31G enters the first multiplexer 32A. The monitoring laser beam M_G guided through the optical fiber 33G via the demultiplexer 31G enters the monitoring light receiver 23.

The demultiplexer 31B divides the B laser beam having entered the proximal end of the optical fiber 29B into a monitoring laser beam (also referred to as monitoring light) M_B of a division ratio n_B and an irradiation laser beam (also referred to as irradiation light) I_B of a division ratio 1−n_B. The irradiation laser beam I_B guided through the optical fiber 29B via the demultiplexer 31B enters a second multiplexer 32B. The monitoring laser beam M_B guided through the optical fiber 33B via the demultiplexer 31B enters the monitoring light receiver 23.

Figure 3A:
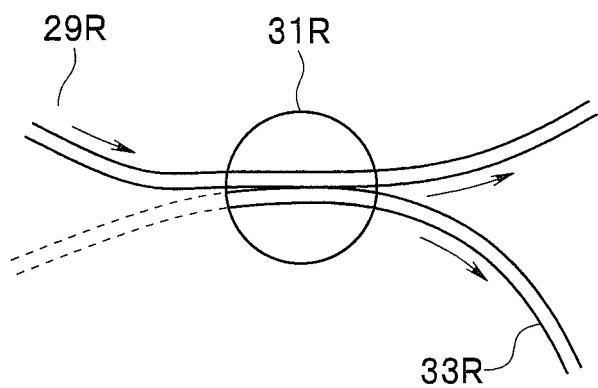
FIG. 3A is a diagram showing an optical fiber in the vicinity of a demultiplexer.

FIG. 3A illustrates one example of the structure of (an area surrounding) the demultiplexer 31R, for example.

As a result of melting extension involving heating, the optical fiber 29R through which the R laser beam is guided is, at the demultiplexer 31R, in close contact with the optical fiber 33R through which the monitoring laser beam M_R is guided. That is, at the demultiplexer 31R, the two optical fibers 29R, 33R in melted states are extended in the longitudinal direction, and respective coatings (clads) thereof in thinner states (compared to those before being extended) are in close contact with each other, and the demultiplexer 31R is formed. As indicated by dotted lines in FIG. 3A, the optical fiber 33R on the left hand of the demultiplexer 31R is removed after the melting extension (because this portion is not used for guiding the monitoring laser beam M_R).

Figure 3B:
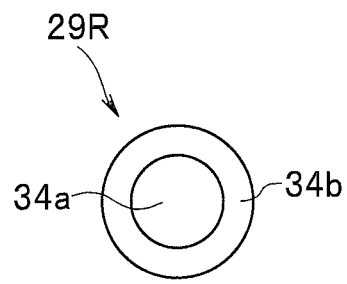
FIG. 3B is a diagram showing a transverse section of the optical fiber at a distal end side portion which has not been subjected to melting extension and is separated from the demultiplexer in FIG. 3A.
Figure 3C:
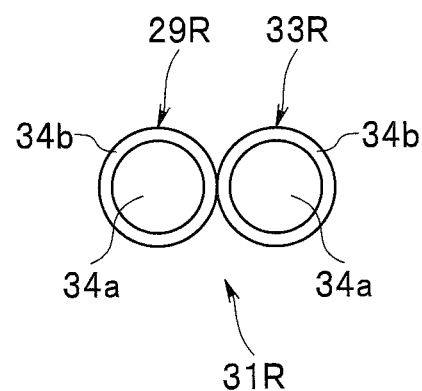
FIG. 3C is a diagram illustrating a transverse section of the optical fiber at the demultiplexer in FIG. 3A.

As illustrated in FIG. 3B, at the proximal end side portion, of the optical fiber 29R, distant from the demultiplexer 31R and having not undergone melting extension, a core 34a is coated with a coating (clad) 34b having a prescribed thickness. As illustrated in FIG. 3C, at the demultiplexer 31R where melting extension with the optical fiber 33R has been performed, the optical fiber 29R and the optical fiber 33R are in close contact with each other with the respective thicknesses of the coatings 34b thereof particularly reduced.

Since the coatings 34b are made thin, the R laser beam guided through the optical fiber 29R from the left hand (proximal end side) to the right hand in FIG. 3A partially leaks, at the demultiplexer 31R, to the optical fiber 33R side so that the monitoring laser beam M_R is generated. The leakage rate depends on the thicknesses of the coatings 34b. The leakage rate also depends on the temperature, the wavelength, or the like.

After passing through the demultiplexer 31R, an irradiation laser beam I_R having a division ratio 1−n_R, which has decreased by the division ratio n_R of the monitoring laser beam M_R, is guided through the optical fiber 29R to the first multiplexer 32A.

The configuration of the demultiplexer 31R has been described with use of FIGS. 3A to 3C. Each of the demultiplexers 31G, 31B has the same configuration.

The first multiplexer 32A multiplexes the irradiation laser beam I_R having been guided through the optical fiber 29R and the irradiation laser beam I_G having been guided through the optical fiber 29G, and an irradiation laser beam I_RG which is a resultant beam having been multiplexed is guided through the optical fiber 35 to the second multiplexer 32B.

The first multiplexer 32A multiplexes the two irradiation laser beams I_R, I_G incident thereon, by using melting extension, etc., as in the demultiplexer 31R.

The second multiplexer 32B generates an irradiation laser beam I_RGB by multiplexing the irradiation laser beam I_RG having been guided through the optical fiber 35 and the irradiation laser beam I_B having been guided through the optical fiber 29B.

Also, the second multiplexer 32B multiplexes the two irradiation laser beams I_RG, I_B incident thereon.

Instead of the two multiplexers of the first multiplexer 32A and the second multiplexer 32B, one multiplexer may be used to generate the irradiation laser beam I_RGB by multiplexing the irradiation laser beams I_R, I_G, I_B having been guided through the optical fibers 29R, 29G, 29B, respectively.

The irradiation laser beam I_RGB generated by the second multiplexer 32B is guided to the optical connector 6 through the optical fiber 36. The optical connector 6 includes a recess portion which holds the distal end portion of the optical fiber 36 and in which the proximal end as an entrance end of the optical fiber 7 facing the distal end surface of the optical fiber 36 is inserted. In the state where the proximal end of the optical fiber 7 is inserted in the recess portion, the irradiation laser beam I_RGB multiplexed by the multiplexer 32B enters the proximal end surface of the optical fiber 7 facing the optical fiber 36, from the distal end surface of the optical fiber 36 forming the exit portion (or the exit surface) for the irradiation laser beam I_RGB.

The distal end surface portion of the optical fiber 36 and the proximal end portion of the optical fiber 7 are provided with respective grin lenses (not illustrated) serving as refractive index distribution lenses which shape light into parallel beams. As a result of provision of the grin lenses, the irradiation laser beam I_RGB emitted from the distal end surface of the optical fiber 36 can be efficiently transmitted to the proximal end surface (incident surface) of the optical fiber 7 as a light guide section for the irradiation light, in the scanning type endoscope 2 (even in a non-contact state where the distal end surface and the proximal end surface are not in contact with each other).

In the present embodiment, the light source unit 3 emits, to the optical fiber 7 of the scanning type endoscope 2, the R, G, B laser beams which are generated by causing intermittent pulse emission at the R_LD 27R, the G_LD 27G, and the B_LD 27B, respectively. The R_LD 27R, the G_LD 27G, and the B_LD 27B are abbreviated as RGB LD 27 or R, G, B_LD 27.

Moreover, the light source unit 3 sequentially emits, as irradiation laser beams I_RGB, the R, G, B laser beams which are emitted at different timings.

The monitoring laser beams M_R, M_G, M_B which are resultant beams having been guided through the optical fibers 33R, 33G, 33B and emitted from respective end surfaces thereof, enter the monitoring light receiver 23. The monitoring laser beams M_R, M_G, M_B are abbreviated as monitoring laser beams M_RGB or M_R, G, B.

The monitoring light receiver 23 collects the monitoring laser beams M_R, G, B emitted from end surfaces which are exit surfaces of the optical fibers 33R, 33G, 33B, by using a lens 37, and receives the monitoring laser beams M_R, G, B at optical detectors 38r, 38g, 38b, respectively. The optical detectors 38r, 38g, 38b respectively output, to the light emission control circuit 25, monitoring light detection signals Sr, Sg, Sb which are photoelectrically converted. The optical detectors 38r, 38g, 38b output, to the light emission control circuit 25, the monitoring light detection signals Sr, Sg, Sb the signal levels of which change corresponding to (the values of) the light quantities of the monitoring laser beams M_R, G, B, respectively.

As indicated by a dotted line in FIG. 2, the optical fibers 33R, 33G, 33B (through which the monitoring laser beams M_R, G, B are guided, respectively) are provided on one monitor substrate 39 that is disposed near the demultiplexers 31R, 31G, 31B.

Further, the monitor substrate 39 is provided with a temperature sensor 40 such as a thermistor for measuring (detecting) the temperature of the monitor substrate 39. Information corresponding to temperature measured by the temperature sensor 40 is inputted to the temperature measuring circuit 24.

The temperature measuring circuit 24 converts the information corresponding to the temperature measured by the temperature sensor 40 into temperature information, and outputs the temperature information to the light emission control circuit 25. Alternatively, the temperature measuring circuit 24 may output the information corresponding to the temperature measured by the temperature sensor 40 to the light emission control circuit 25, and the light emission control circuit 25 may have a function of converting an output signal from the temperature sensor 40 into temperature information.

At the demultiplexers 31R, 31G, 31B which the R, G, B laser beams from the R, G, B_LD 27 respectively enter, when the temperature changes, the values of the division ratios change (due to slight change in the wavelengths of spectra of the R, G, B laser beams or due to the temperature characteristics of the coatings 34b, etc.) (see a LUT 42 in FIG. 4). Accordingly, when the temperature changes, the light quantity of the irradiation laser beam I_RGB also changes. In addition, it has been found that the values of the division ratios change by change in the spectra of the R, G, B laser beams from the LDs 27 caused by the temperature change.

When the temperature changes, the light emission control circuit 25 controls the light emission quantities of the R, G, B LD 27 with reference to information about the division ratios at the changed temperature.

Even when the temperature changes, the light emission control circuit 25 performs control such that the light quantity of the irradiation laser beam I_RGB, which is irradiation light (or emitted light) emitted from the light source unit 3 to the external scanning type endoscope 2, satisfies a predetermined condition of the laser safety standards.

In other words, the light emission control circuit 25 performs control such that, at any measured temperature, the light quantity of the irradiation laser beam I_RGB as irradiation light emitted from the light source unit 3 to the external scanning type endoscope 2 satisfies the predetermined condition of the laser safety standards.

The light emission control circuit 25 controls the light emission quantities of R, G, B_LD 27, which are three light emitting elements constituting the pigtail LD unit 21, by using control signals Cr, Cg, Cb on the basis of the monitoring light detection signals Sr, Sg, Sb.

In the present embodiment, the control signals Cr, Cg, Cb are drive currents Di_R, Di_G, Di_B for causing light emission from the R, G, B_LD 27, respectively.

The light emission quantities of the R, G, B_LD 27 change in accordance with the values of the drive currents Di_R, Di_G, Di_B applied thereto, respectively. For example, the light emission quantity of the R_LD 27R increases with increase of the value of the drive current Di_R applied thereto. The G_LD 27G and the B_LD 27B also have the same characteristics.

Further, in order to perform control to satisfy the predetermined condition as described above, the light emission control circuit 25 includes a memory 41 that holds (or stores) information including parameters required for the control. The memory 41 stores therein in advance information such as that shown in FIG. 4.

The memory 41 holds, as a lookup table (LUT) 42, for example, information about the respective division ratios at the three demultiplexers 31R, 31G, 31B as parameters which change in accordance with the temperature, and also stores therein in advance a maximum peak light quantity value 43 which is a basic condition for satisfying the predetermined condition of the laser safety standards irrespective of the temperature, and (information about) a maximum average light quantity value 44 in a predetermined time period (more specifically, 250 ms).

The maximum peak light quantity value 43 and the maximum average light quantity value 44 in the predetermined time period correspond to maximum values to be satisfied by the irradiation laser beam I_RGB emitted from the optical combiner 22 of the light source unit 3 to the optical fiber 7 of the scanning type endoscope 2. The memory 41 stores a value greater than 30 W, for example, as the maximum peak light quantity value 43 and stores a value of 5 mW, for example, as the maximum average light quantity value 44.

As shown in FIG. 4, as the R division ratio (n_R), the G division ratio (n_G), and the B division ratio (n_B) at the demultiplexers 31R, 31G, 31B at 40° C. which is the temperature during normal driving, 0.30, 0.30, and 0.30 are designated (set), respectively, in the LUT 42. At 25° C. which is the temperature immediately after driving, for example, the R division ratio (n_R), the G division ratio (n_G), and the B division ratio (n_B) are 0.20, 0.15, and 0.10, respectively. In this way, the LUT 42 stores information about the temperature—the R division ratio, the G division ratio, and the B division ratio (also referred to as temperature-RGB division ratio information) as parameters. In FIG. 4, specific values of the RGB division ratios at the temperature other than 25° C. or 40° C. are omitted.

As described above, the LUT 42 stores, as parameters, information about a plurality of temperatures in the demultiplexers 31R, 31G, 31B and the RGB division ratios at each of the temperatures.

(As can be seen from the configuration in FIG. 2) the light quantity of the irradiation laser beam I_RGB is not directly monitored, but the light quantities of the monitoring laser beams M_R, G, B, which are obtained by demultiplexing (division) from the irradiation laser beams I_RGB by the demultiplexers 31R, 31G, 31B, are monitored, and thereby, the light emission quantities of the R, G, B LDs 27, that is, the R_LD 27R, the G_LD 27G, and the B_LD 27B are controlled.

The conditions of the maximum peak light quantity value 43 and the maximum average light quantity value 44 (in the predetermined time period) remain unchanged even when the temperature changes. However, when the temperature changes, the values of the division ratios at the demultiplexers 31R, 31G, 31B change, as shown in the LUT 42 in FIG. 4.

Accordingly, in the present embodiment, the light emission control circuit 25 calculates the maximum (monitor) peak light quantity value 43c of the monitoring laser beams M_R, G, B in the case of the maximum peak light quantity value 43a of the irradiation laser beam I_RGB, with reference to the values of the division ratios in the initial state.

The light emission control circuit 25 controls the maximum peak light quantity values of the R, G, B LDs 27 (forming the R, G, B light emitting elements) such that the maximum peak light quantity values of the monitoring laser beams M_R, G, B are lower than a maximum peak light quantity value 43c that corresponds to the case of the maximum peak light quantity value 43 (of the irradiation light).

As a result of this control, the maximum peak light quantity values of the R, G, B_LD 27 can be adjusted (controlled) such that the maximum peak light quantity value of the irradiation laser beam I_RGB is lower than a maximum peak light quantity value 43a (such that one of the two predetermined conditions is satisfied).

Similarly, at the initial state temperature, the light emission control circuit 25 calculates the maximum average (monitor) light quantity value 44c of the monitoring laser beams M_R, G, B in the case of the maximum average light quantity value 44a of the irradiation laser beam I_RGB, with reference to the values of the division ratios.

Then, the light emission control circuit 25 controls the maximum average light quantity value of the R, G, B_LD 27 such that the maximum average light quantity value of the monitoring laser beams M_R, G, B becomes lower than the maximum average light quantity value 44c.

As a result of this control, the maximum average light quantity values of the R, G, B_LD 27 can be set (controlled) such that the maximum average light quantity value of the irradiation laser beam I_RGB is lower than the maximum average light quantity value 44a (such that one of the two predetermined conditions is satisfied).

As described above, the memory 41 may store a value greater than 30 W as the maximum peak light quantity value 43 and a value of 5 mW as the maximum average light quantity value 44. Alternatively, the memory 41 may store a value smaller than the value greater than 30 W by Δ1 (e.g. approximately 0.3 W) and a value smaller than 5 mW by Δ2 (e.g. 0.5 mW) such that the light emission quantities can be controlled with slightly relaxed strictness (accuracy).

Also, for example, in the initial state, the memory 41 may store light emission quantities in the initial state (an R light emission quantity, a G light emission quantity, and a B light emission quantity in the initial state) 45 set as the light emission quantities of the R, G, B_LD 27. In the initial state, white balance adjustment is performed. Therefore, the light emission quantities in the initial state can be also regarded as the light emission quantities after white balance adjustment. Since white balance adjustment is performed at the initial state temperature, the initial state light emission quantities are also equivalent to light emission quantities at the initial state temperature.

The light emission control circuit 25 controls the light emission quantities of the R_, G_, B_LD 27 through the control signals Cr, Cg, Cb, respectively, with reference to the information stored in the memory 41. The control signals Cr, Cg, Cb are formed by the drive currents Di_R, Di_G, Di_B, as described above.

At the initial state temperature, the light emission control circuit 25 sets (adjusts) the light emission values in the initial state 45 of the R, G, B_LD 27 by using the initial state control signals Cr, Cg, Cb, respectively, such that the light quantity of the irradiation laser beams I_RGB emitted from the optical combiner 22 (to the optical fiber 7 of the scanning type endoscope 2) becomes an appropriate light quantity lower than the maximum peak light quantity value 43 and the maximum average light quantity value 44 (the predetermined conditions are satisfied), and stores the set light emission values in the initial state 45 in the memory 41.

After the adjustment, the light emission quantities of the R, G, B_LD 27 are controlled by monitoring of the light quantities of the monitoring laser beams M_R, G, B such that the light quantity of the irradiation laser beam I_RGB does not change from the appropriate light quantity even when the temperature changes. Accordingly, for example, in a case where the temperature reaches a temperature in normal driving, the value of the light quantity of the irradiation laser beam I_RGB is controlled to maintain the value equal to the initial state temperature. At the temperature in normal driving, the R, G, B drive currents to be obtained when light emission at the R, G, B_LD 27 is caused so as to provide an appropriate light quantity of the irradiation laser beam I_RGB, may be checked in advance and be stored in the memory 41. Further, at other temperatures, the R, G, B drive currents to be obtained when the light emission at the R, G, B_LD 27 is caused, may be also checked in advance and stored in the memory 41 (see FIG. 8A).

Figure 5:
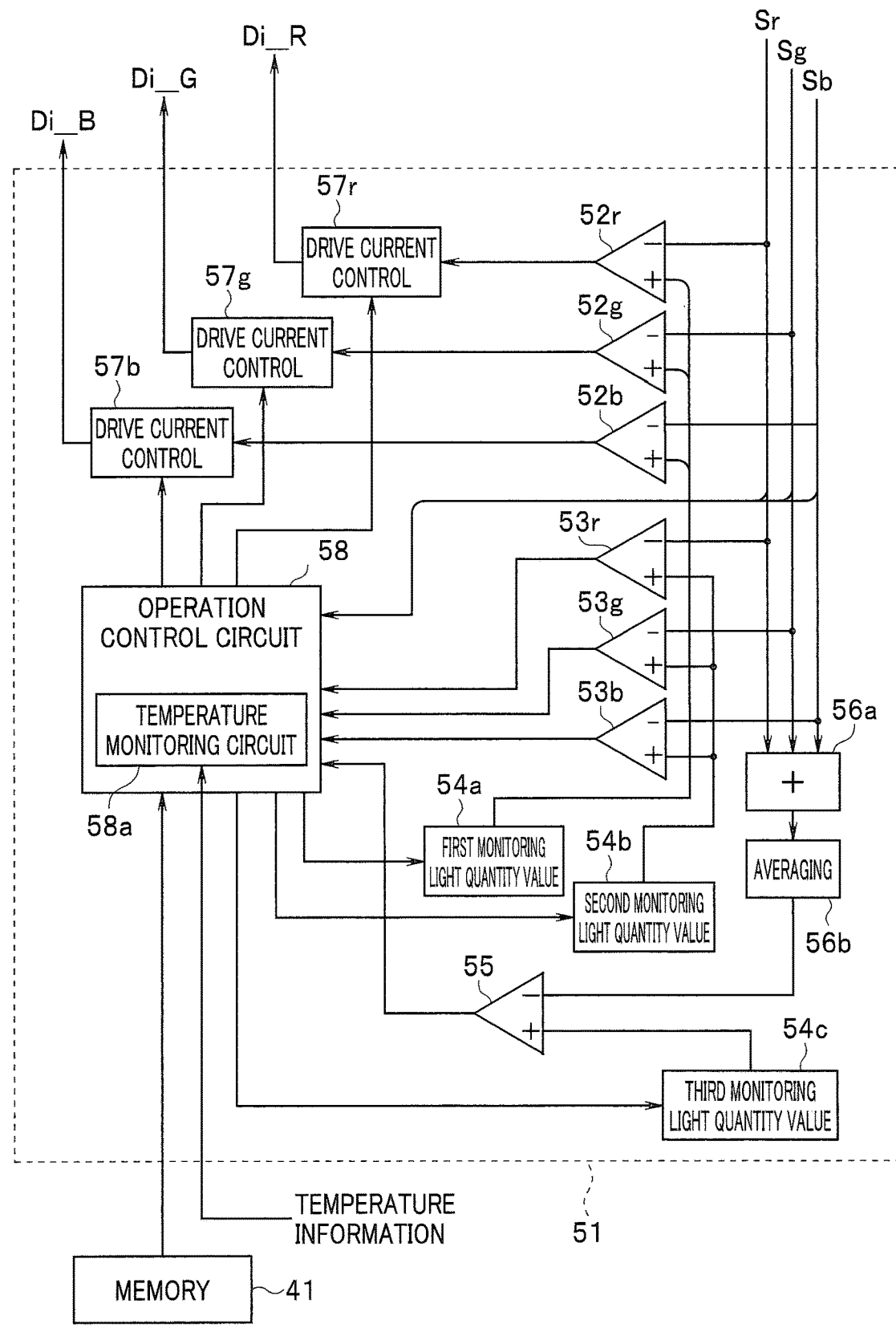
FIG. 5 is a diagram showing one example of a specific configuration of a comparison operation circuit.

The light emission control circuit 25 performs control to maintain the appropriate light quantities in the state satisfying the predetermined condition, while monitoring the state in which the light quantity of the irradiation laser beam I_RGB satisfies the predetermined condition of the laser safety standards. In order to perform such a control, the light emission control circuit 25 includes a comparison operation circuit 51 shown in FIG. 5, for example.

The comparison operation circuit 51 has a first function of controlling the light emission quantities of the R, G, B_LD 27 such that the light quantity of the irradiation laser beam I_RGB becomes an appropriate light quantity in accordance with a set value (set within a range satisfying the predetermined condition), and has second and third functions of monitoring whether or not the predetermined condition (or a condition close thereto) is satisfied.

The first function is configured with use of subtraction circuits (or difference circuits) 52r, 52g, 52b, and the second and third functions are configured with use of first comparison circuits 53r, 53g, 53b and a second comparison circuit 55.

As described later, the comparison operation circuit 51 has a monitoring function of monitoring temporal change in the monitoring light detection signals Sr, Sg, Sb, determining, when the monitoring light detection signals Sr, Sg, Sb change by a threshold or greater while the temperature has not changed, for example, deviation from an allowable monitoring condition, and generating an alarm signal or an error signal.

The monitoring light detection signals Sr, Sg, Sb (obtained by photoelectric conversion of the received monitoring laser beams M_R, G, B) are applied to one input terminal of each of the subtraction circuits 52$r$, 52$g$, 52$b$ constituting the comparison operation circuit 51 and the first comparison circuits 53$r$, 53$g$, 53$b$, respectively, and a first monitoring light quantity value 54$a$ and a second monitoring light quantity value 54$b$ (which are set in accordance with measured temperature) are applied to other input terminal. The first monitoring light quantity value 54$a$, the second monitoring light quantity value 54$b$, and a third monitoring light quantity value 54$c$ which is described later are stored in a register (or a memory) in the comparison operation circuit 51.

An average value signal obtained by adding the monitoring light detection signals Sr, Sg, Sb through an addition circuit 56$a$ and by averaging the signals in a predetermined time period through an averaging circuit 56$b$ is applied to one input terminal of the second comparison circuit 55, and the third monitoring light quantity value 54$c$ (set in accordance with the measured temperature) is applied to the other input terminal.

Subtraction signals obtained by the subtraction circuits 52$r$, 52$g$, 52$b$ subtracting the monitoring light detection signals Sr, Sg, Sb from the first monitoring light quantity values 54$a$ are inputted to drive current control circuits 57$r$, 57$g$, 57$b$, respectively, and the drive current control circuits 57$r$, 57$g$, 57$b$ apply, to the R, G, B_LD 27, the drive currents Di_R, Di_G, Di_B corresponding to output signals (subtraction signals) from the subtraction circuits 52$r$, 52$g$, 52$b$, so that the light emission quantities are controlled.

The first monitoring light quantity values 54$a$ correspond to set target values of the light quantities of the monitoring laser beams M_R, G, B. The drive current control circuits 57$r$, 57$g$, 57$b$ control the light emission quantities of the R, G, B_LD 27 by using the drive currents Di_R, Di_G, Di_B in accordance with the subtraction signals such that the light quantities of the monitoring laser beams M_R, G, B reach the respective set target values.

For example, when the subtraction signal from the subtraction circuit 52$r$ is 0, the drive current control circuit 57$r$ maintains the value of the immediately preceding drive current Di_R, and when the subtraction signal becomes a value greater than 0, the drive current control circuit 57$r$ reduces the value of the drive current Di_R, and when the subtraction signal becomes a value smaller than 0, the drive current control circuit 57$r$ increases the value of the drive current Di_R. The same operation is also performed in the remaining subtraction circuits 52$g$, 52$b$. The light emission quantities of the R, G, B_LD 27 are controlled as described above.

The first monitoring light quantity value 54$a$ in the initial state is equal to a set target value corresponding to the case of the light quantity value of the irradiation laser beam I_RGB. When the division ratios at the demultiplexers 31R, 31G, 31B change due to temperature change, the first monitoring light quantity values 54$a$ on which the changed division ratios are reflected are set.

The first comparison circuits 53$r$, 53$g$, 53$b$ and the second comparison circuit 55 output respective signals of comparison results to an operation control circuit 58.

Information about the temperature measured by the temperature sensor 40 is inputted to the operation control circuit 58. A temperature monitoring circuit 58$a$ in the operation control circuit 58 monitors whether or not the inputted temperature has changed. When the temperature from the temperature monitoring circuit 58$a$ has changed by a (preset) threshold or greater, the operation control circuit 58 adjusts (controls) the light emission quantities of the R, G, B_LD 27 through the drive current control circuits 57$r$, 57$g$, 57$b$ with reference to the division ratios corresponding to the changed temperature.

The monitoring light detection signals Sr, Sg, Sb are inputted to the operation control circuit 58, and the operation control circuit 58 monitors temporal change in the monitoring light detection signals Sr, Sg, Sb.

As described above, the first monitoring light quantity value 54$a$ in the initial state is the light emission value in the initial state 45 or the monitoring light quantity value corresponding to the light quantity value of the irradiation laser beam I_RGB in the initial state. (In this case, in order to maintain the fixed value of the irradiation laser beam I_RGB with respect to the temperature change), when the values of the division ratios at the demultiplexers 31R, 31G, 31B change in accordance with the temperature, the first monitoring light quantity value 54$a$ also changes.

The operation control circuit 58 sets the first monitoring light quantity value 54$a$ in a variable manner with reference to the values of the division ratios at the demultiplexers 31R, 31G, 31B which change in accordance with the measured temperature. In setting of the first monitoring light quantity value 54$a$ after temperature change, reference is made to the values of the division ratios at the demultiplexers 31R, 31G, 31B prior to the temperature change (for example, see FIG. 7A). Also, the operation control circuit 58 also sets the second monitoring light quantity value 54$b$ and the third monitoring light quantity value 54$c$ in a variable manner.

The drive current control circuits 57$r$, 57$g$, 57$b$ control the light emission quantities of the R, G, B_LD 27 such that the light emission quantities match the first monitoring light quantity values 54$a$ set in a variable manner in accordance with the values of the division ratios at the demultiplexers 31R, 31G, 31B, as described above.

On the other hand, the second monitoring light quantity value 54$b$ and the third monitoring light quantity value 54$c$ are monitoring light quantity values (to be monitored by the monitoring light receiver 23) respectively corresponding to the light emission values in the initial state 45 set in the initial state and the maximum average light quantity values 44 in this case. Since the light emission value in the initial state 45 is set to be lower than the maximum peak light quantity value 43, the light emission value in the initial state 45 is set to a light emission quantity equivalent to the light emission value in the initial state 45 smaller than the maximum peak light quantity value 43 by Δ (>Δ1), for example.

Also in this case, when the temperature changes, the values of the division ratios at the demultiplexers 31R, 31G, 31B change. Therefore, as in the initial state, the second monitoring light quantity value 54$b$ and the third monitoring light quantity value 54$c$ are monitoring light quantity values for monitoring whether or not a condition of being lower than the maximum peak light quantity value 43 and the maximum average light quantity value 44 is satisfied.

In a case where a signal applied to an input terminal(s) of second comparison circuits 53r, 53g, 53b or a third comparison circuit 55 is a comparison signal having a monitoring light quantity value lower than the value of the monitoring light quantity applied to the input terminal(s) of the other circuit(s) (i.e. a case where a predetermined condition is satisfied), the operation control circuit 58 causes (controls) the drive current control circuits 57r, 57g, 57b to operate in accordance with output signals from the first comparison circuits (or subtraction circuits) 52r, 52g, 52b.

In contrast, when a signal to be applied to an internal terminal(s) of the second comparison circuits 53r, 53g, 53b or the third comparison circuit 55 is a comparison signal having a light quantity value equal to or greater than the monitoring light quantity value to be applied to an input terminal(s) of the other circuit(s), the operation control circuit 58 controls the drive current control circuits 57r, 57g, 57b to forcibly reduce the drive currents Di_R, Di_G, Di_B.

In a state immediately after the state of the comparison signal is assumed, each of the second and third monitoring light quantity values may be set to a value close to a boundary of the predetermined condition without deviating from the predetermined conditions.

When the state of the comparison signal is assumed, the operation control circuit 58 may output (issue) an alarm signal to the image generating circuit 16, such that the display device 5 may display that the light emission quantity of the light source unit 3 has reached a value close to the maximum value of the laser safety standards or that the light emission quantity has reached a value close to the maximum value, and therefore, has been forcibly reduced.

An example in which the operation control circuit 58 is provided in the light emission control circuit 25 has been described. However, the operation control circuit 58 may be provided in the monitoring light receiver 23. Further, as indicated by a two-dot chain line in FIG. 1, the light emission control circuit 25 may include the monitoring light receiver 23 (having the operation control circuit 58 incorporated therein).

The light source unit 3 of the present embodiment forming the light source device for an endoscope of the present invention includes: one (e.g. the G_LD 27G) of the R_LD 27R, the G_LD 27G, and the B_LD 27B forming a first light emitting element which emits a first laser beam of a first spectrum responding to a control signal (one of Cr, Cg, and Cb) forming a first control signal; one (e.g. the B_LD 27B) of the R_LD 27R, the G_LD 27G, and the B_LD 27B forming a second light emitting element which emits a second laser beam of a second spectrum responding to a control signal (one of Cr, Cg, and Cb) forming a second control signal; the optical combiner 22 forming a beam combiner which the first laser beam and the second laser beam enter, which transmits a laser beam having a spectrum component based on a synthesized spectrum of the first spectrum and the second spectrum, and emits the laser beam as irradiation light to the scanning type endoscope 2 forming the endoscope, and which emits a part of the laser beam as monitoring light having an intensity of a predetermined division ratio; the temperature sensor 40 and the temperature measuring circuit 24 forming a temperature measuring section for measuring the temperature of the beam combiner; and the light emission control circuit 25 having the memory 41 for holding parameters related to the division ratios at a plurality of temperatures and forming a light emission control section which outputs the first control signal and the second control signal in accordance with the parameter corresponding to the temperature, and thereby, performs control such the maximum light quantity of the irradiation light satisfies a predetermined condition.

Next, the operation in the present embodiment is described with reference to the flowchart in FIG. 6.

As illustrated in FIG. 1, the scanning type endoscope 2 is connected to the body device 4 including the light source unit 3. Thereafter, at the first step S1, in order to set (determine) the R, G, B light emission quantities of the R, G, B_LD 27 in the initial state, the light emission control circuit 25 acquires information about the temperature obtained by the temperature sensor 40 (through the temperature measuring circuit 24).

At the following step S2, the light emission control circuit 25 acquires, from (the LUT 42 in) the memory 41, the division ratios at the demultiplexers 31R, 31G, 31B at the above temperature.

At step S3, the light emission control circuit 25 reads out (acquires) the maximum peak light quantity value 43 and the maximum average light quantity value 44 of the irradiation laser beam I_RGB from the memory 41. Further, the maximum peak light quantity values of the R, G, B_LD 27 corresponding to the read maximum peak light quantity value 43 and the read maximum average light quantity value 44, and the respective light quantity values of the monitoring laser beams M_R, G, B in the case of the maximum average light quantity value are calculated.

In other words, the light emission control circuit 25 calculates the maximum peak light quantity values and the maximum average light quantity values of the R, G, B_LD 27 and the monitoring laser beams M_R, G, B corresponding to the maximum peak light quantity value 43 and the maximum average light quantity value 44.

Moreover, (the operation control circuit 58 in) the light emission control circuit 25 stores, in a register, the calculated maximum peak light quantity values and the maximum average light quantity values of the monitoring laser beams M_R, G, B as second monitoring light quantity values and third monitoring light quantity values, respectively.

At the following step S4, the light emission control circuit 25 sets initial state light quantity values, which are light emission values for causing pulse light emission at the R, G, B_LD 27, under the condition of being lower than the second monitoring light quantity value and the third monitoring light quantity value. When this setting is performed, the operation control circuit 58 calculates, by using the values of the division ratios, monitoring laser light quantity values in the case of detection of the monitoring laser beams M_R, G, B, and stores the monitoring laser light quantity values as first monitoring light quantity values in the register (in FIG. 7A described later, the values are M1r, M1g, and M1b at 40° C., and are values each including a coefficient at 25° C.).

At the following step S5, white balance adjustment is performed. A white object is prepared as a reference for white balance adjustment, and the light emission control circuit 25 causes pulse light emission at the R, G, B_LD 27 by the respective initial state light quantity values.

The signal light detecting unit 13 detects signal light reflected by the white object, the image generating circuit 16 generates an image signal, and an image of the white object is displayed on the display device 5. The white balance adjusting circuit 16a in the image generating circuit 16 adjusts a gain of an amplifier in the white balance adjusting circuit 16a so as to provide a white balance state in which R, G, B color signal levels in the image signal are equal to one another. In this way, white balance adjustment is completed.

When white balance adjustment is performed, the adjustment may be performed by changing the light emission quantities of the R, G, B_LD 27.

The light emission values of the R, G, B_LD 27 in the initial state may be determined by white balance adjustment, and the determined values may be stored as light emission values in the initial state 45 in the memory 41.

At the following step S6, the scanning type endoscope 2 is inserted into a body cavity of an inspection subject, for example, such that the subject 8 in the body cavity can be observed.

At the following step S7, (a temperature monitoring circuit 58*a* of the operation control circuit 58 in) the light emission control circuit 25 regularly monitors the temperature information (obtained by the temperature sensor 40). At the following step S8, (the operation control circuit 58 in) the light emission control circuit 25 determines whether or not the temperature has changed from the previous temperature by a threshold or greater.

When the determination result of the determination process at step S8 shows that the temperature has changed, the light emission control circuit 25 acquires, at the following step S9, the values of the division ratios at the changed temperature, as in step S2.

At the following step S10, (the operation control circuit 58 in) the light emission control circuit 25 updates the first monitoring light quantity value 54*a*, the second monitoring light quantity value 54*b*, and the third monitoring light quantity value 54*c* by using the values of the changed division ratios.

For example, in a case where the initial state temperature, which is 25° C., has been increased, when the RGB division ratios at the demultiplexers 31R, 31G, 31B are changed to increase (as shown in the LUT 42 in FIG. 4), the values of the first monitoring light quantity value 54*a*, the second monitoring light quantity value 54*b*, and the third monitoring light quantity value 54*c* are updated to become greater values in accordance with this change.

When the monitoring light quantity values are updated as described above, (the operation control circuit 58 in) the light emission control circuit 25 regularly monitors whether or not the irradiation laser beam I_RGB (emitted from the light source unit 3 to the optical fiber 7 of the scanning type endoscope 2) satisfies the predetermined condition, on the basis of the second monitoring light quantity value 54*b* and the third monitoring light quantity value 54*c*, at the changed temperature in the same manner as that at the temperature prior to the change.

In order to satisfy the predetermined condition at the changed temperature, at step S11, (the operation control circuit 58 in) the light emission control circuit 25 controls the light emission quantities of the R, G, B_LD 27 on the basis of the first monitoring light quantity value 54*a* such that the light emission quantity of the irradiation laser beam I_RGB is kept at the initial state light emission quantity.

At the following step S12, the light emission control circuit 25 determines whether or not an instruction to end the inspection is given by an operator as a user. When no instruction to end the inspection is given, the process returns to step S7. When an instruction to end the inspection is given, the process in FIG. 6 is ends.

When the determination process at step S8 determines that the temperature has not changed, (the operation control circuit 58 in) the light emission control circuit 25 monitors temporal change in the average value of the signal levels of the monitoring light detection signals Sr, Sg, Sb, at step S13. At the following step S14, (the operation control circuit 58 in) the light emission control circuit 25 determines whether or not the temporal change is equal to or greater than an allowable threshold. When the determination result indicates that change equal to or greater than the threshold has not occurred, the process returns to step S7.

Figure 6:
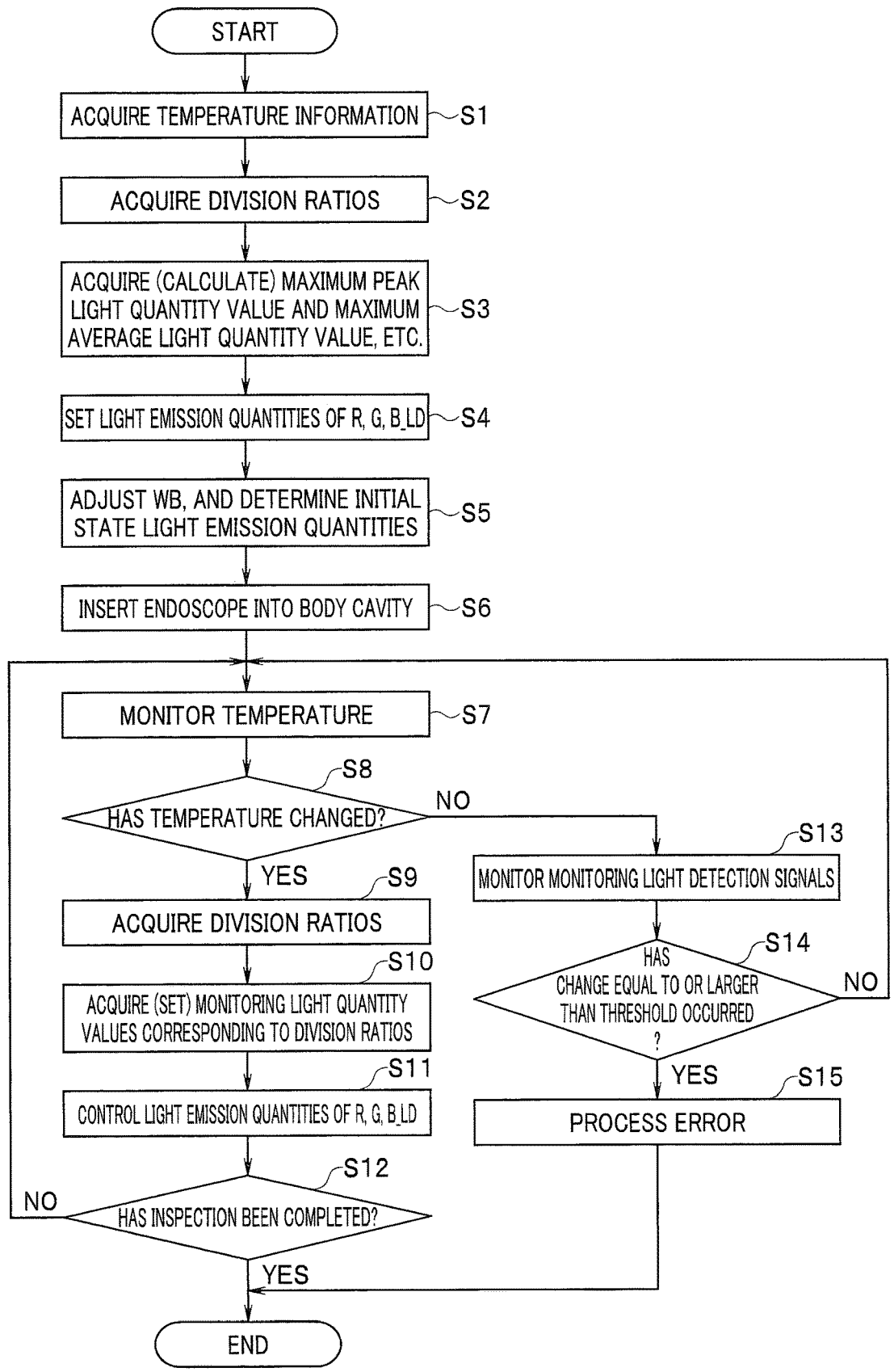
FIG. 6 is a flowchart showing processes in the first embodiment.

In contrast, when the determination result indicates that change equal to or greater than the threshold has occurred, at step S15, the light emission control circuit 25 determines that an error has occurred and processes the error that has occurred, and the process in FIG. 6 ends. For example, when an error has occurred, the light emission control circuit 25 outputs a signal indicating occurrence of the error to the image generating circuit 16 and the display device 5 displays occurrence of the error.

In the present embodiment in which the aforementioned operation is performed, even when the values of the division ratios at the demultiplexers 31R, 31G, 31B change due to temperature change, the light emission quantities of the light emitting elements are controlled according to the change in the values of the division ratios such that the light quantity of emission light to be emitted to the scanning type endoscope 2 forming the endoscope satisfies the predetermined condition.

Consequently, according to the present embodiment, even when the temperature changes, the state where the light quantity of irradiation light emitted to the endoscope satisfies the predetermined condition can be maintained.

Also, according to the present embodiment, any temperature control device for holding the temperature of the demultiplexers 31R, 31G, 31B, etc. at which the division ratios changes in accordance with the temperature is not required. Accordingly, the problem of the cost increase to a temperature control device can be solved.

In addition, since any temperature control device is not required, energy saving can be achieved. In order to hold a fixed temperature by means of a temperature control device, energy for heating is necessary when the actual temperature is lower than the fixed temperature (to be held), or a Peltier element, etc. which has a function of performing cooling (absorbing heat) but is expensive, needs to be driven when the actual temperature is higher than the fixed temperature. According to the present embodiment, a Peltier element, etc. which is expensive is not required and energy saving can be achieved.

In addition, according to the present embodiment, even when the temperature changes, control is performed to maintain the light quantity of irradiation light to be emitted to the scanning type endoscope 2. Therefore, when a white balance state is set in the initial setting, the white balance state can be maintained (even if a temperature change has occurred).

Moreover, since the present embodiment does not need to keep the temperature fixed, the present embodiment can be used in a temperature environment the temperature of which greatly changes.

Furthermore, in the present embodiment, rather than the light quantities of the irradiation laser beam I_RGB to be emitted (through the demultiplexers 31R, 31G, 31B), the light quantities of the monitoring laser beams M_R, G, B obtained by division at the demultiplexers 31R, 31G, 31B are monitored, and thereby, the light emission quantities of the R, G, B_LD 27 are adjusted by the RGB drive currents (Di_R, Di_G, Di_B).

Accordingly, irrespective of the characteristics of the light emission quantities of the R, G, B_LD 27 which change in accordance with temperature change (even if the RGB drive currents are fixed), the light emission quantities of the R, G, B_LD 27 can be controlled (by adjustment of the RGB drive currents) such that the light quantity of the irradiation laser beam I_RGB is appropriately maintained.

As can be seen from the operation in the first embodiment, in order to maintain the appropriate (fixed) light quantity of the irradiation laser beam I_RGB even when temperature change occurs, the RGB drive currents Di_R, Di_G, Di_B are increased/reduced such that the light quantities of the monitoring laser beams M_R, G, B become equal to the first monitoring light quantity values (as photoelectrically converted signal values) corresponding to set target values which are set in a variable manner in accordance with the temperature change.

To this end, the first monitoring light quantity values set at each temperature may be stored in a table 59 in advance in the memory 41.

Figure 7A:
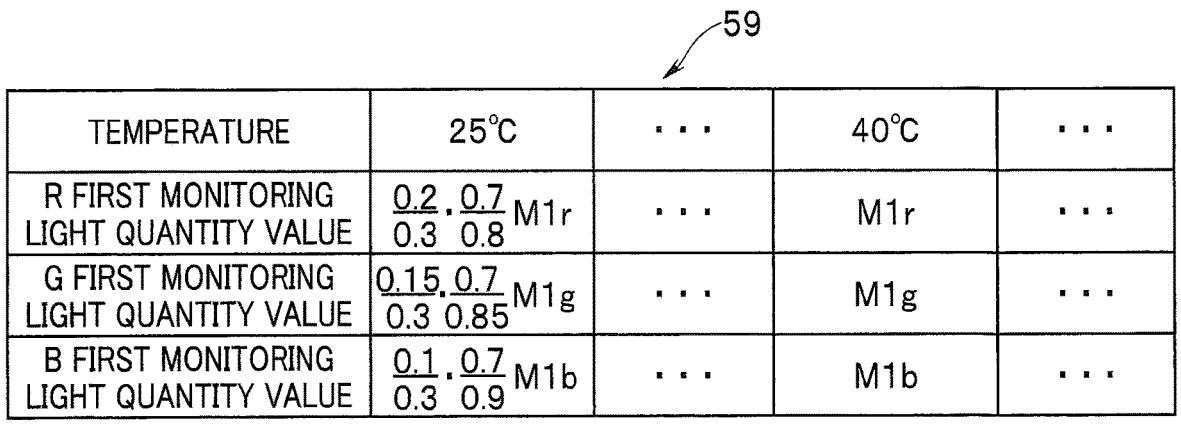
FIG. 7A is a diagram showing a table in which a plurality of temperatures and RGB monitoring light quantity values set by the values of RGB division ratios being taken into consideration, are stored in association with each other in the first embodiment.

FIG. 7A shows an example of the table 59 of the RGB first monitoring light quantity values which are set for each of a plurality of temperatures.

In the example shown in FIG. 7A, for example, M1r, M1g, M1b are shown as the R, G, B first monitoring light quantity values at 40° C., respectively. The R, G, B first monitoring light quantity values M1r, M1g, M1b at 40° C. are set in accordance with the values of 0.3, 0.3, 0.3, respectively, which are the R, G, B division ratios at the same temperature.

At 25° C., the R, G, B first monitoring light quantity values are set to (0.2/0.3)×(0.7/0.8)M1r, (0.15/0.3)×(0.7/0.85)M1g, and (0.1/0.3)×(0.7/0.9)M1b, respectively. In the example shown in FIG. 7A, the values at 25° C. are set with use of 40° C. as the reference temperature. Alternatively, the R, G, B first monitoring light quantity values at another temperature may be set with use of 25° C. as the reference temperature.

In other words, the R, G, B first monitoring light quantity values are set such that the light quantity of the irradiation laser beam I_RGB at one reference temperature T1 satisfies the laser safety standards and is suited for observation, etc.

For example, when the temperature changes to T2, the R, G, B first monitoring light quantity values at T2 are set in accordance with the R, G, B first monitoring light quantity values at the reference temperature T1. In this way, even when the temperature changes, the light quantity of the irradiation laser beam I_RGB is adjusted to an appropriate fixed light quantity in accordance with the R, G, B first monitoring light quantity values. As can be seen from the example in FIG. 7A, the R, G, B first monitoring light quantity values at T2 are set while the values of the division ratios at T1 and T2 are taken into consideration.

In the case where the R, G, B first monitoring light quantity values are set as shown in FIG. 7A, the light quantity of the irradiation laser beam I_R when the light quantity of the monitoring laser beam M_R is controlled to the R first monitoring light quantity value M1r at 40° C., for example, is obtained by (0.7/0.3)M1r.

When the temperature changes to 25° C., the light quantity of the irradiation laser beam I_R when the light quantity of the monitoring laser beam M_R is controlled to the R first monitoring light quantity value (0.2/0.3)×(0.7/0.8)M1r becomes (0.8/0.2) times of the above value, that is, (0.7/0.3)M1r, which is equal to the light quantity of the irradiation laser beam I_R at 40° C. Namely, even when the temperature changes, control to maintain the appropriate light quantity of the irradiation laser beam I_RGB can be performed by use of the R, G, B first monitoring light quantity values which are set while the R, G, B division ratios which change in accordance with temperature change are taken into consideration.

Information about the light emission quantities (light emission intensities) obtained when light emission at the R, G, B_LD 27 is caused in accordance with FIG. 7A may be stored in the memory 41.

Figure 7B:
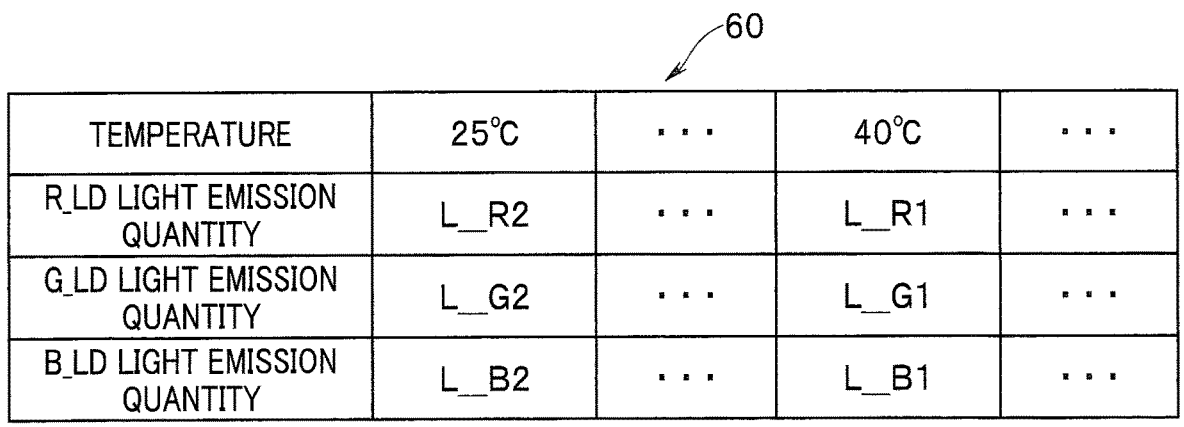
FIG. 7B is a diagram showing a table which corresponds to FIG. 7A, and in which the plurality of temperatures and RGB monitoring light quantity values set by the values of the RGB division ratios being taken into consideration, are stored in association with each other.

FIG. 7B shows a table 60 of the light emission quantities (light emission intensities) of the R, G, B_LD 27 corresponding to FIG. 7A. In the table 60, the light emission quantities of the R, G, B_LD 27 at 40° C., for example, are stored as L_R1, L_G1, and L_B1, and the light emission quantities of the R, G, B_LD 27 at 25° C., for example, are stored as L_R2, L_G2, and L_B2. L_R1, L_G1, and L_B are parameter values related to the light quantities or light intensities of the R, G, B laser beams.

With use of the R, G, B first monitoring light quantity values M1r, M1g, M1b in FIG. 7A, the values of L_R1, L_G1, and LB1 are obtained by M1r+(0.7/0.3)×M1r, M1g+(0.7/0.3)×M1g, and M1b+(0.7/0.3)×M1b, respectively.

Similarly, with use of the R, G, B first monitoring light quantity values at 25° C. in FIG. 7A which are denoted by M2r, M2g, M2b, the values of L_R2, L_G2, L_B2 are obtained by M2r+(0.8/0.2)×M2r, M2g+(0.85/0.15)×M2g, and M2b+(0.9/0.1)×M2b, respectively.

Then, the light emission quantities of the R, G, B_LD 27 may be adjusted to the light emission quantities of the R, G, B_LD shown in FIG. 7B by the RGB drive currents as the RGB control signals.

The light emission quantities of the R, G, B_LD 27 may be controlled by use of a part of the processing in the flowchart shown in FIG. 6. For example, after the light emission quantities of the R, G, B_LD 27 is set in the initial state so as to satisfy the predetermined condition, the drive current control circuits 57r, 57g, 57b may control the light emission quantities of the R, G, B_LD 27 by the drive currents Di_R, Di_G, Di_B with use of the first monitoring light quantity value 54a (rather than the second monitoring light quantity value 54b or the third monitoring light quantity value 54c) such that the light quantities of the monitoring laser beams M_R, G, B are maintained at the first monitoring light quantity value 54a.

Next, a first modification of the first embodiment is described (the tables 59, 60 in FIGS. 7A, 7B are included in the first embodiment).

A light source unit of the first modification of the first embodiment includes, for example, in the pigtail LD unit 21, a temperature sensor 61 which is indicated by a dotted line in the light source unit 3 in FIG. 2, and which detects (measures) the temperatures of the R, G, B LDs 27. A detection signal from the temperature sensor 61 is inputted to the temperature measuring circuit 24 as indicated by a dotted line. The temperature measuring circuit 24 converts information corresponding to the temperature measured by the temperature sensor 61 into temperature information, and outputs the temperature information to the light emission control circuit 25.

The temperature sensor 61 is used for correcting temperature-dependent changes of the light emission quantities of the R, G, B LDs 27. The light emission quantities of the R, G, B LDs 27 change in accordance with the temperature change even if the drive currents are not changed.

For this reason, in the present modification, the R drive current, the G drive current, and the B drive current are stored, in the memory 41 or the like, as RGB drive currents for causing light emission in the R, G, B_LD 27 in accordance with the temperatures of the R, G, B_LD 27. In addition, the LUT 42, etc. in the first embodiment is stored in the memory 41.

Figure 8A:
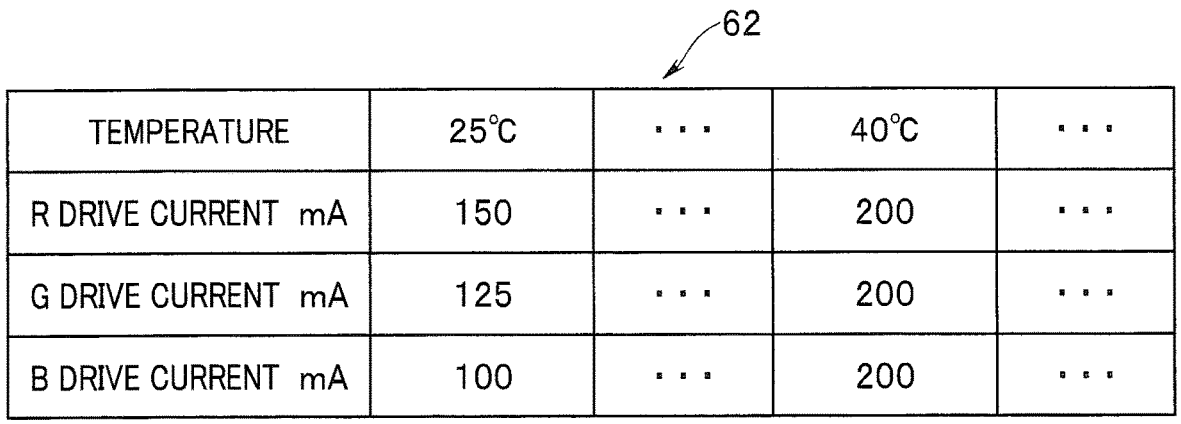
FIG. 8A is a diagram showing a table of RGB drive currents associated with temperatures stored in the memory.

FIG. 8A shows a table 62 for the R drive current, the G drive current, and the B drive current as the RGB drive currents stored in the memory 41 such that the RGB drive currents are associated with the temperature.

The values in FIG. 8A shows one example of the RGB drive currents. FIG. 8A shows that, for example, in a case where each of the R drive current, the G drive current, and the B drive current are set to 200 mA at 40° C., the R drive current, the G drive current, and the B drive current may be set to 150 mA, 125 mA, and 100 mA, respectively, at 25° C. in order to maintain the same light emission quantities.

Accordingly, when each of the R drive current, the G drive current, and the B drive current at 40° C. is set to 200 mA, the set drive currents can be used as they are, and when the drive currents are changed to a different value (e.g. 180 mA which is not equal to 200 mA), the drive currents at other temperatures also need to be changed.

Figure 8B:
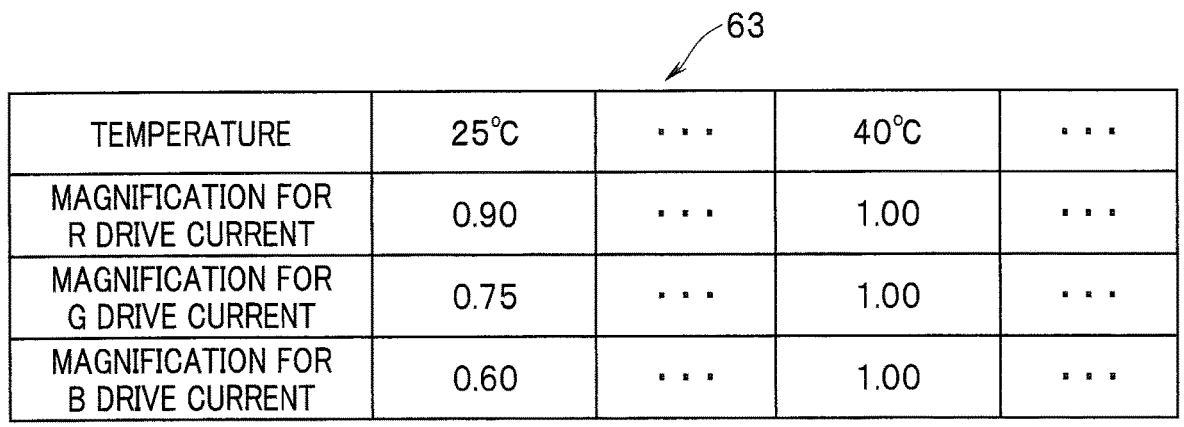
FIG. 8B is a diagram showing a table of the values of magnifications for RGB drive currents at reference temperatures, which are associated with temperatures stored in the memory.

Instead of the RGB drive currents associated with the temperature in the manner as shown in FIG. 8A, a table 63 of magnifications with respect to the RGB drive currents at a reference temperature may be stored as shown in FIG. 8B.

In the table 63 in FIG. 8B, the RGB drive currents set at 40° C., for example, are defined as RGB drive currents at a reference temperature. The table 63 shows that, when the temperature detected (measured) by the temperature sensor 61 is 25° C., the RGB drive currents are preferably set to 0.90 times of the R drive current at 40° C., 0.75 times of the G drive current at 40° C., and 0.60 times of the B drive current at 40° C., respectively. The table 63 in FIG. 8B has an advantage that, even when a drive current set at a reference temperature changes, a drive current at a different current can be easily calculated with use of information about the magnifications.

Both the tables 62, 63 may be provided to allow a user to select either FIG. 8A or FIG. 8B. Except for this, the configuration of the present modification is identical to that of the first embodiment.

According to the present modification, when the temperature changes, setting of the RGB drive currents for causing light emission at the R, G, B_LD 27 by the same light emission quantities, is easy. Except for this, the present modification provides effects similar to those by the first embodiment.

In the present modification, the two temperature sensors 40, 61 are provided. However, only one of temperature sensors may be provided and the temperature of a measurement target which would be measured by the other temperature sensor may be estimated from the temperature measured by the one temperature sensor.

Second Embodiment

Figure 9:
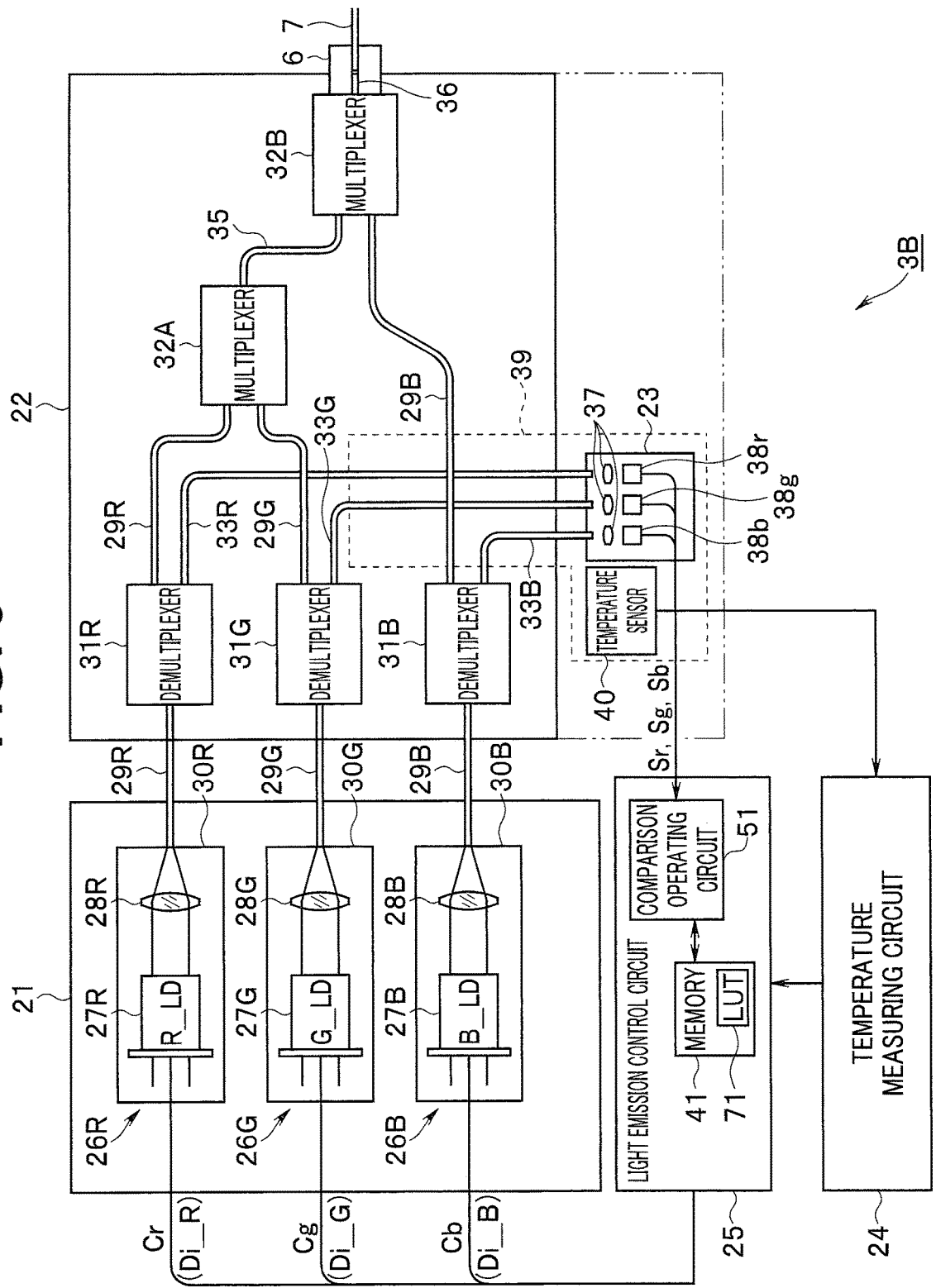
FIG. 9 is a diagram illustrating the configuration of a light source unit of a second embodiment of the present invention.

Next, a second embodiment of the present invention is described. FIG. 9 illustrates a light source unit 3B of the second embodiment. In the present embodiment, the demultiplexers 31R, 31G, 31B and the R, G, B_LD 27 are disposed at positions close to each other. For example, the temperature sensor 40 disposed near the demultiplexers 31R, 31G, 31B can measure (detect) the temperatures of the demultiplexers 31R, 31G, 31B and the temperatures of the R, G, B_LD 27.

As described above, the light emission quantities of the R, G, B_LD 27 change in accordance with the temperature (even when the RGB drive currents are not changed). For this reason, when the light emission quantities of the R, G, B_LD 27 change in accordance with the temperature, the emission quantity of the irradiation laser beam I_RGB changes.

Figure 10:
FIG. 10 is a diagram showing a lookup table storing the values of RGB division ratios and the values of RGB light emission quantity change magnifications corresponding to a plurality of temperatures.

To this end, in the present embodiment, instead of the LUT 42 of the first embodiment, a LUT 71 shown in FIG. 10 is stored in the memory 41. The LUT 71 stores information about light emission quantity change magnifications at different temperatures wherein each of the magnifications for the light emission quantities of the R, G, B_LD 27 at a reference temperature is defined as 1, in addition to the information about the RGB division ratios in the LUT 42. In FIG. 10, the light emission ratios of the R, G, B_LD 27 are denoted by L_R, L_G, and L_B, respectively.

Except for this, the configuration of the present embodiment is identical to that of the first embodiment.

In the first embodiment, since the values of the division ratios change when the temperature changes, the light emission quantities of the R, G, B_LD 27 are adjusted by the RGB drive currents Di_R, Di_G, Di_B with use of the information about the division ratios at the changed temperature based on monitoring of the monitoring laser beams M_R, G, B such that the irradiation laser beam I_RGB satisfies the laser safety standards and the light quantity equal to that in the initial state is maintained.

Also in this case, the light emission quantities of the R, G, B_LD 27 change in accordance with the temperature. However, in the first embodiment, even when the light emission quantities change dependently on the temperature, control is performed so as to reliably satisfy the laser safety standards based on the monitoring laser beams M_R, G, B.

In the present embodiment, information about the change magnification of the light emission quantity with respect to the reference temperature is stored in advance so that, when the temperature changes, an appropriate light emission quantity is easy to set more smoothly.

The operation in the present embodiment is described in comparison with that of the first embodiment, for example.

For example, it is assumed that, in each of the first embodiment and the present embodiment, the light emission quantities of the R, G, B_LD 27 at 25° C. as the initial state temperature are set to light emission quantities L_R(25), L_G(25), L_B(25) corresponding to (appropriate) light emission quantities within a range of the state where the irradiation laser beam I_RGB satisfies the laser safety standards. The light emission quantity L_R(25) represents the light emission quantity of the R_LD 27R at 25° C.

In this case, the division ratios at the demultiplexers 31R, 31G, 31B are 0.20, 0.15, and 0.10, respectively. Accordingly, the light quantity of the irradiation laser beam I_RGB (i.e. I_R, I_G, and I_B) is obtained by L_R(25)×(1−0.20), L_G(25)×(1−0.15), and L_B(25)×(1−0.10), and the light quantity of the monitoring laser beams M_R, M_G, and M_B is obtained by L_R(25)×0.20, L_G(25)×0.15, and L_B(25)×0.10.

In this state, the light quantity of the monitoring laser beams M_R, G, B is adjusted (to a first monitoring light quantity value), and accordingly, the light emission quantities L_R(25), L_G(25), L_B(25) of the R, G, B_LD 27 are adjusted by the RGB drive currents Di_R, Di_G, Di_B.

It is assumed that operation is performed by setting made in the initial state, and then, the temperature is increased to 40° C., for example. In this case, the division ratios at the demultiplexers 31R, 31G, 31B change from 0.20, 0.15, and 0.10 to 0.30, 0.30, and 0.30, respectively.

In the first embodiment, the RGB drive currents Di_R, Di_G, Di_B are adjusted such that the light quantity of the irradiation laser beam I_RGB remain unchanged and the light quantity of the monitoring laser beams M_R, G, B become equal to the first monitoring light quantity value at 40° C., so that the light emission quantities L_R(40), L_G (40), and L_B(40) of the R, G, B_LD 27 are set.

In this case, the light emission quantities L_R(40), L_G (40), L_B(40) of the R, G, B_LD 27 are not directly set.

In contrast, in the present embodiment, reference to the information about the change magnifications of the light emission quantities L_R(40), L_G(40), L_B(40) of the R, G, B_LD 27 before and after temperature change can be made.

Accordingly, as a result of increase of the light emission quantities by 1.0/0.85, 1.0/0.90, 1.0/0.95, for example, setting to the light emission quantities L_R(40), L_G(40), L_B(40) in the case of temperature change can be more quickly made.

When the temperature is changed to another temperature, the same operation is also performed. According to the present embodiment, even when the division ratios at the demultiplexers 31R, 31G, 31B change due to temperature change, the light emission quantities of the R, G, B_LD 27 can be controlled so as to satisfy the condition of the laser safety standards, as in the first embodiment. Further, when adjustment to a white balance state is performed, the white balance state can be maintained irrespective of temperature change.

Moreover, regarding the characteristics of the light emission quantities of the R, G, B_LD 27 as light sources which change in accordance with temperature change, the light emission quantities of the R, G, B_LD 27 can be controlled so as to satisfy the laser safety standards, as in the first embodiment.

Furthermore, by use of the information about the light emission quantity change magnifications, the light emission quantities of the R, G, B_LD 27 can be more quickly set to appropriate light emission quantities.

Figure 11:
FIG. 11 is a diagram showing a lookup table storing the values of RGB drive currents at the plurality of temperatures obtained by taking the RGB division ratios into consideration.

In a modification of the present embodiment, instead of the LUT 71 shown in FIG. 10, a LUT 72 of the RGB drive currents Di_R, Di_G, Di_B which define the light emission quantities of the R, G, B_LD 27 by taking temperature change into consideration, as shown in FIG. 11 may be provided.

In the LUT 72 shown in FIG. 11, the values of the RGB drive currents may be set by the RGB division ratios which change in accordance with temperature change and change in the light emission quantities of the RGB_LD which change in accordance with temperature change being taken into consideration.

When control to maintain the RGB drive currents in the LUT 72 at each temperature is performed, a parameter for correction regarding change in the light emission quantities of the RGB_LD in accordance with temperature change does not need to be separately provided. Accordingly, the capacity of the memory can be saved. When control without using information about the RGB division ratios which change in accordance with temperature change may be performed, the capacity of the memory can be further saved.

In the above first embodiment, etc., the example has been described in which, in a case where the white balance state is set in the initial state, control is performed so as to maintain the appropriate fixed light quantity of the irradiation laser beam I_RGB even when the temperature changes. However, the present invention is not limited to this case. Alternatively, control close to this control may be performed.

For example, control may be performed such that, when the light quantity value of the irradiation laser beam I_RGB which is to be controlled is closer to a boundary value of the predetermined condition of the maximum peak light quantity value 43, etc., a range of an allowable deviation quantity is made smaller.

In other words, in a light quantity range sufficiently smaller than the maximum peak light quantity value 43, the light quantity value of the irradiation laser beam I_RGB may be changeable rather than being fixed. However, when the light quantity value of the irradiation laser beam I_RGB is changed, the change may be made so as to hold the white balance state.

More specifically, when the light quantity value of the irradiation laser beam I_RGB is increased or reduced, the increase or reduction may be done by values proportional to the value of the light quantity of (I_R, I_G, I_B of) the irradiation laser beam I_RGB in the state prior to the change. As a result of such control, the value of the light quantity can be increased or reduced while an effect of suppressing change from the white balance state prior to the change in the values of the light quantity of the irradiation laser beam I_RGB is maintained.

The light emission quantities of the R, G, B_LD 27 may be changed by the RGB drive currents as the control signals such that the value of the light quantity of the irradiation laser beam I_RGB is changed in the aforementioned manner.

Moreover, in each of the aforementioned embodiments (including the modifications), for example, since noise of the optical detectors 38r, 38g, 38b on the monitor substrate 39 changes depending on the temperature (more specifically, the noise increases with increase in the temperature), the temperatures of the demultiplexers 31R, 31G, 31B disposed near the monitor substrate 39 may be estimated from the noise level while no temperature sensor is provided. The temperatures of the demultiplexers 31R, 31G, 31B and the temperatures of the demultiplexers 31R, 31G, 31B may be used for estimation.

The aforementioned embodiments, etc. may be partially combined with one another.

The present invention is not limited to the aforementioned embodiments, and various changes and modifications, etc. can be made within the scope of the present invention.

What is claimed is:

1. A light source device for an endoscope, the device comprising:
   a first light source configured to emit a first laser beam of a first spectrum responding to a first control signal;
   a second light source configured to emit a second laser beam of a second spectrum responding to a second control signal;
   a demultiplexer configured to divide the first laser beam and the second laser beam into two divided first laser beams and into two divided second laser beams, respectively, each at a predetermined division ratio;
   a beam combiner configured to combine one of the two divided first laser beams and one of the two divided second laser beams into a combined laser beam, the beam combiner being configured to transmit the combined laser beam having a spectrum component based on a synthesized spectrum of the first spectrum and the second spectrum, and emit the combined laser beam as irradiation light to the endoscope, and to emit an other one of the two divided first laser beams and an other one of the two divided second laser beams as monitoring light to a light detector, a ratio of intensities of the irradiation light and the monitoring light being equal to the predetermined division ratio;

a temperature sensor configured to measure a temperature of the beam combiner;

a memory holding a parameter concerning the division ratio at a plurality of temperatures, and a light emission controller configured to perform control, by outputting the first control signal and the second control signal based on the parameter corresponding to the temperatures, such that a maximum light quantity of the irradiation light satisfies a predetermined condition.

2. The light source device for an endoscope according to claim 1, further comprising a comparison operation circuit configured to receive the monitoring light, monitor whether or not the monitoring light satisfies a monitoring condition including the predetermined condition, and issue an alarm signal when the monitoring light fails to satisfy the monitoring condition.

3. The light source device for an endoscope according to claim 1, wherein the memory holds the parameter which is set such that an average light quantity of the irradiation light per 250 ms does not exceed 5 mW and such that a maximum peak light quantity during pulse lighting does not exceed 30 W.

4. The light source device for an endoscope according to claim 1, further comprising an R light source configured to emit an R laser beam of an R spectrum having a peak within a red wavelength region responding to an R control signal, wherein the first light source is a G light source configured to emit a G laser beam of a G spectrum having a peak within a green wavelength region responding to a G control signal, the second light source is a B light source configured to emit a B laser beam of a B spectrum having a peak within a blue wavelength region responding to a B control signal, the beam combiner
generates R monitoring light and R irradiation light by dividing the R laser beam at an R division ratio,
generates G monitoring light and G irradiation light by dividing the G laser beam at a G division ratio,
generates B monitoring light and B irradiation light by dividing the B laser beam at a B division ratio,
emits the monitoring light formed of the R monitoring light, the G monitoring light, and the B monitoring light, and
emits the irradiation light obtained by multiplexing the R irradiation light, the G irradiation light, and the B irradiation light, the memory holds an R parameter regarding the R division ratio, a G parameter regarding the G division ratio, and a B parameter regarding the B division ratio at each of a plurality of temperatures, and the light emission controller outputs the R control signal in accordance with the R parameter, outputs the G control signal based on the G parameter, and outputs the B control signal in accordance with the B parameter.

5. The light source device for an endoscope according to claim 4, wherein in a case where a white balance state is set at a first temperature with predetermined light quantities of the R irradiation light, the G irradiation light, and the B irradiation light, in response to temperature change from the first temperature, the light emission controller controls light quantities of the R irradiation light, the G irradiation light, and the B irradiation light based on the R parameter, the G parameter, and the B parameter stored in the memory so as to suppress change from the white balance state.

6. The light source device for an endoscope according to claim 4, wherein the memory further holds an R intensity parameter regarding an emission intensity of the R laser beam, a G intensity parameter regarding an emission intensity of the G laser beam, and a B intensity parameter regarding an emission intensity of the B laser beam, at each of a plurality of temperatures, and the light emission controller outputs the R control signal which changes also in accordance with change in the R intensity parameter, outputs the G control signal which changes also in accordance with change in the G intensity parameter, and outputs the B control signal which changes also in accordance with change in the B intensity parameter.

7. The light source device for an endoscope according to claim 4, further comprising a temperature monitoring circuit configured to monitor whether or not the temperature measured by the temperature sensor changes by a threshold or greater, wherein when the temperature changes by the threshold or greater, the light emission control section controller:

reads out, from the memory, a first parameter and a second parameter as parameters, values of which change in accordance with a first temperature which is the temperature in the case of change made by the threshold or greater and a second temperature which is the temperature prior to the change, and controls light emission quantities of the R laser beam, the G laser beam, and the B laser beam emitted by the R light source, the G light source, and the B light source, by the R control signal, the G control signal, and the B control signal based on the first parameter and the second parameter, such that the light quantity of the irradiation light at the first temperature which is the temperature in the case of the change made by the threshold or greater, matches the light quantity of the irradiation light at the second temperature set within a range satisfying the predetermined condition.

8. The light source device for an endoscope according to claim 7, wherein the memory stores R, G, B monitoring light quantity values which are set target values of the light quantity of the monitoring light corresponding to the light quantities of the irradiation light of the R laser beam, the G laser beam, and the B laser beam at each of a plurality of temperatures, and the light emission controller controls light emission quantities of the R light source, the G light source, and the B light source, by the R control signal, the G control signal, and the B control signal corresponding to a subtraction value of the R, G, B monitoring light quantity values and the light quantity of the monitoring light corresponding to the R, G, B monitoring light quantity values, such that the subtraction value becomes 0.

9. The light source device for an endoscope according to claim 1, wherein the temperature sensor is disposed near the beam combiner or near the first light source and the second light source.

10. The light source device for an endoscope according to claim 1, wherein the temperature sensor is disposed near the first light source and the second light source, and a temperature of the beam combiner is estimated from a temperature measured by the temperature sensor.

11. The light source device for an endoscope according to claim 1, further comprising a temperature monitoring circuit configured to monitor whether or not the temperature measured by the temperature sensor changes by a threshold or greater, wherein when the temperature changes by the threshold or greater, the light emission controller:

reads out, from the memory, a first parameter and a second parameter as parameters, values of which change in accordance with a first temperature which is the temperature in the case of change made by the threshold or greater and a second temperature which is the temperature prior to the change, and controls respective light emission quantities of the first laser beam and the second laser beam emitted by the first light source and the second light source, by the first control signal and the second control signal based on the first parameter and the second parameter, such that a light quantity of the irradiation light at the first temperature in the case of the change made by the threshold or greater matches a light quantity of the irradiation light at the second temperature set within a range satisfying the predetermined condition.

12. The light source device for an endoscope according to claim 11, wherein the memory stores first and second monitoring light quantity values at each of a plurality of temperatures, which are set target values of the light quantities of the monitoring light corresponding to the light quantity of the irradiation light of the first laser beam and the second laser beam, and the light emission controller controls light emission quantities of the first light source and the second light source, by the first control signal and the second control signal corresponding to a subtraction value of the first and second monitoring light quantity values and respective light quantities of the monitoring light corresponding to the first and second monitoring light quantities, such that the subtraction value becomes 0.

\* \* \* \* \*